United States Patent [19]
Izmailov et al.

[11] Patent Number: 5,599,434
[45] Date of Patent: Feb. 4, 1997

[54] ELECTROPHORESIS GELS AND GEL HOLDERS HAVING ADHESIVE AFFIXED FIBER SPACERS AND METHOD OF MAKING SAME

[75] Inventors: Alexandre M. Izmailov, Toronto; Henryk Zaleski, Niagara Falls, both of Canada

[73] Assignee: Visible Genetics Inc., Toronto, Canada

[21] Appl. No.: 571,132

[22] Filed: Dec. 12, 1995

[51] Int. Cl.$^6$ .................. G01N 27/26; G01N 27/447
[52] U.S. Cl. .................. 204/470; 204/619; 204/620
[58] Field of Search .................. 204/456, 459, 204/461, 465, 466, 467, 606, 612, 616, 617, 618, 619, 620

[56] References Cited

U.S. PATENT DOCUMENTS

| | | | |
|---|---|---|---|
| 4,704,198 | 11/1987 | Ebersole et al. | 204/469 |
| 4,790,919 | 12/1988 | Baylor, Jr. | 204/616 |
| 4,811,218 | 3/1989 | Hunkapiller et al. | 364/413.01 X |
| 4,823,007 | 4/1989 | Hanson | 250/580 |
| 4,863,647 | 9/1989 | Baylor, Jr. | 264/425 |
| 4,929,329 | 5/1990 | Danby et al. | 204/608 |
| 5,047,135 | 9/1991 | Nieman | 204/619 |
| 5,062,942 | 11/1991 | Kambara et al. | 204/612 |
| 5,071,531 | 12/1991 | Soane | 204/612 |
| 5,073,246 | 12/1991 | Chu et al. | 204/619 |
| 5,091,652 | 2/1992 | Mathies et al. | 250/458.1 |
| 5,092,973 | 3/1992 | Zare et al. | 204/452 |
| 5,108,179 | 4/1992 | Myers | 356/344 |
| 5,119,316 | 6/1992 | Dam et al. | 364/498 |
| 5,122,345 | 6/1992 | Tabor et al. | 422/116 |
| 5,141,868 | 8/1992 | Shanks et al. | 435/287.9 |
| 5,164,066 | 11/1992 | Yetman et al. | 204/619 |
| 5,186,807 | 3/1993 | Sanford et al. | 204/618 |
| 5,192,408 | 3/1993 | Scott | 204/470 X |
| 5,192,412 | 3/1993 | Kambara et al. | 204/612 |
| 5,202,010 | 4/1993 | Guzman | 204/601 |
| 5,209,831 | 5/1993 | MacConnell | 204/616 |
| 5,324,401 | 6/1994 | Yeung et al. | 204/452 |
| 5,338,426 | 8/1994 | Shigeura et al. | 204/461 |
| 5,356,776 | 10/1994 | Kambara et al. | 435/6 |

FOREIGN PATENT DOCUMENTS

93/00986  1/1993  WIPO.

OTHER PUBLICATIONS

Maniatis, Chapter 5, "Gel Electrophoresis" no date available.

Ansorge et al., "Thermally Stabilized Very Thin (0.02–0.3 mm) Polyacrylamide Gels for Electrophoresis", *J. Chromatography* 202: 45–53 no month available (1980).

Current Protocols in Molecular Biology, "Electrophoretic Separation of Proteins", pp. 10.2.1–10.2.21 no month available (1991).

*Primary Examiner*—Donald R. Valentine
*Assistant Examiner*—John S. Starsiak, Jr.
*Attorney, Agent, or Firm*—Oppedahl & Larson

[57] ABSTRACT

Gel holders for electrophoresis gels are made using fibers, particularly glass fibers, which are affixed to the substrates forming the gel holder using an adhesive. These gel holders can be made by placing a plurality of adhesive-coated fibers between a first planar substrate and a second planar substrate; and applying pressure to the outside of the substrates to adhere the fibers to the first and second substrates. This forms a gel chamber between the first and second substrates which has a thickness defined by diameter of the fibers. Alternatively, uncoated fibers may be laid down in pairs, with a line of adhesive disposed between each fiber of the pair. When the adhesive is cured, it binds the fibers in position as spacers. At the same time, the fibers isolate the adhesive from the gel compartment. In this way, interference of components of the adhesive with the polymerization of the a gel in the gel chamber can be avoided. Gel holders formed using either of these methods may be filled immediately with a gel forming solution such as a polyacrylamide, or they may be stored indefinitely and used as needed.

36 Claims, 5 Drawing Sheets

5,599,434

ELECTROPHORESIS GELS AND GEL HOLDERS HAVING ADHESIVE AFFIXED FIBER SPACERS AND METHOD OF MAKING SAME

BACKGROUND OF THE INVENTION

DNA sequencing may be carried out using automated systems designed for laboratory application. Methods and apparatus for sequencing of DNA are described in U.S. Pat. Nos. 4,811,218; 4,823,007; 5,062,942; 5,091,652; 5,119,316 and 5,122,345, which are incorporated herein by reference.

The general methodology employed in these systems involves breaking up the sample DNA using restriction endonucleases; amplifying (for example with PCR) the restriction fragment of interest; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

In performing a nucleic acid sequence analysis on a gel, the characteristics of the gel, including the size and thickness, impact the time and cost required to do the analysis. Since it is desirable to reduce the time and cost of sequencing analyses in order to improve the available of sequencing as a diagnostic tool, it would be advantageous to have a gel which permitted analysis of very small quantities of oligonucleotide fragments in a short period of time. It would further be advantageous to have a disposable, single use gel holder which could be manufactured on a large scale which when filled with a gel would provide these desirable characteristics.

Persons making the very thin gels which can achieve the type of short analysis times and high throughput desired for sequence analysis face several challenges. Significant among these is developing a fabrication technique which defines and maintains a very uniform spacing between the substrates surrounding the gel, so that the gel itself is of uniform thickness. U.S. Pat. Nos. 4,929,329 and 5,164,066, which are incorporated herein by reference, disclose the formation of electrophoresis gels using thin films (on the order of 0.10 to 0.02 inches thick), for example made from mylar, or nylon monofilaments as spacers between front and back plates. The spacers are not adhered to the plates, but are simply placed between the two plates and held in place using clamps while the space between the two plates is filled with gel forming solution. After polymerization, the polymerized gel holds the two plates, as well as the spacers in place.

The method of forming electrophoresis gels disclosed in these patents has several drawbacks. First of all, because the spacers have to be positioned and then held in place during the gel-filling operation, the resulting gels are not well suited to large scale production. Furthermore, because gels have short shelf lives, once prepared, and because it is the gel which holds the plates and the spacers together, assembly of the device must occur at the point of use. This too argues against the use of spacers as disclosed in these patents in the production of significant numbers of gels, or in the production of disposable, single use gel holders.

It an object of the present invention to provide disposable, single use gel holders having a very thin gel chamber of uniform thickness, which can be easily manufactured.

It is a further object of this invention to provide a method of making disposable, single use gel holders having a very thin gel chamber of uniform thickness, which can be easily manufactured.

It is a further object of this invention to provide electrophoresis gels formed within disposable, single use gel holders having a very thin gel chamber of uniform thickness, which can be easily manufactured.

SUMMARY OF THE INVENTION

These and other objects of the invention can be achieved by forming a gel holder for an electrophoresis gel using fibers, particularly glass fibers, affixed to the substrates forming the gel holder using an adhesive. Thus, one aspect of the invention is a method comprising the steps of:

(a) placing a plurality of adhesive-coated fibers between a first planar substrate and a second planar substrate;

(b) applying pressure to the outside of the substrates to adhere the fibers to the first and second substrates, thereby forming a gel chamber between said first and second substrates, said gel chamber having a thickness defined by interior core of the fibers.

Alternatively, uncoated fibers may be laid down in pairs, with a line of adhesive disposed between each fiber of the pair. When the adhesive is cured, it binds the fibers in position as spacers and it also fixes the first and second substrates with respect to each other. At the same time, the fibers isolate the adhesive from the gel compartment. In this way, interference of components of the adhesive with the polymerization of the a gel in the gel chamber can be avoided.

Gel holders formed using either of these methods may be filled immediately with a gel forming solution such as a polyacrylamide, or they may be stored indefinitely and used as needed. Thus, further aspects of the invention are gel holders, and electrophoresis gel products comprising (a) a first planar substrate;

(b) a second planar substrate; and (c) a plurality of fibers disposed singly or in pairs between the first and second planar substrates. The fibers are adhered to the substrate using an adhesive so that the fibers and the first and second planar substrates, in concert, define a gel chamber having a thickness defined by the diameter of the fibers. In the finished electrophoresis gel, this chamber is filled with a polymerized gel such as a polyacrylamide gel.

DETAILED DESCRIPTION OF THE INVENTION

Figure 1A:
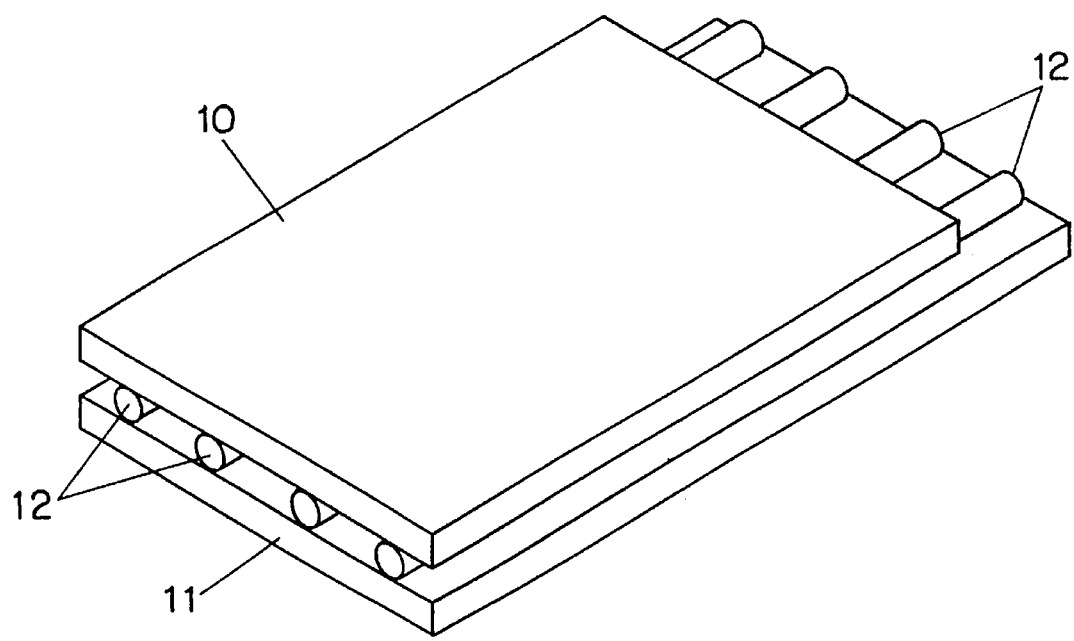
FIGS. 1A and 1B shows a first embodiment of a gel holder in accordance with the present invention.
Figure 1B:
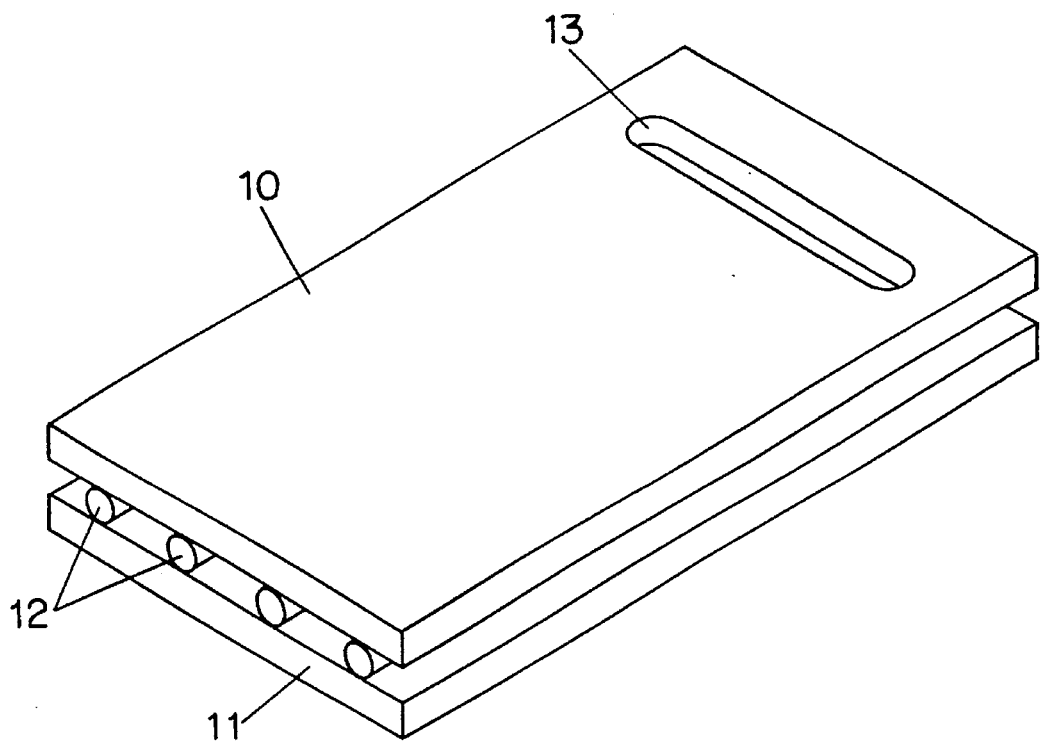

FIG. 1 shows a first embodiment of a gel holder in accordance with the present invention. The gel holder is formed from a top substrate 10, a bottom substrate 11 and a plurality of fibers 12, which may be circular in cross-section as shown or have an ovoid or rectangular cross-section. The fibers 12 are disposed parallel to one another and to opposing edges of the substrates 10, 11 and extend from one end of the substrates to the other. The bottom substrate 11 may extend beyond the top substrate 10 at one end of the gel holder as shown to facilitate loading of electrophoresis samples, in which case the fibers may end even with the top substrate or extend out onto the bottom substrate as shown in FIG. 1A. Alternatively, an opening 13 may be cut near one end of the top substrate for this purpose. (FIG. 1B)

Figure 2A:
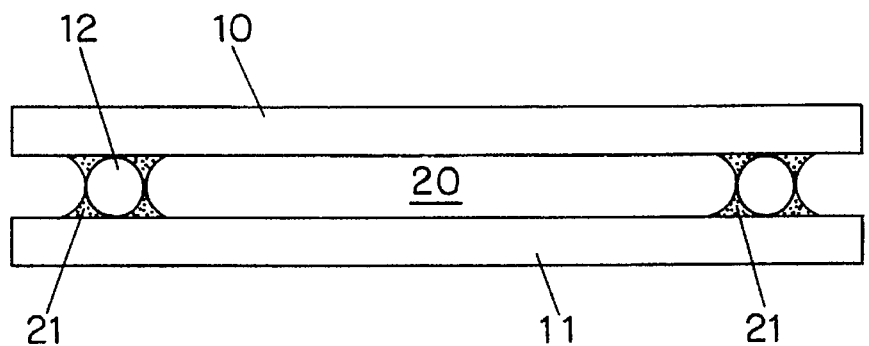
FIGS. 2A and 2B show end views of two embodiments of a gel holder in accordance with the invention.

FIG. 2A shows the bottom end of a gel holder having two fibers rather than the four shown in FIG. 1 in greater detail. The fibers 12 are in contact with the top and bottom substrates 10, 11, and are adhered to the substrates with an adhesive 21. The fibers 12 and the top and bottom substrates 10, 11 in concert define a chamber 20 which is filled with an electrophoresis gel.

Figure 2B:
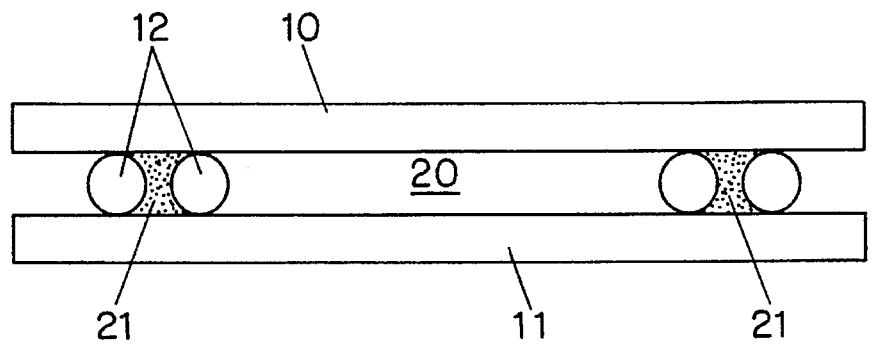

FIG. 2B shows an end view of an alternative embodiment of the invention. In this case, the fibers 12 are laid down between the substrate in pairs, and affixed in place with a line of adhesive filling the space between the two fibers. This space is small, relative to the separation between adjacent pairs of fibers, and is preferably the space left when two fibers are placed side-by-side nearly in contact with one another as shown in FIG. 2B.

The adhesive substance may be any adhesive which is capable of forming a bond between the materials chosen for the substrate and the fibers. In a preferred embodiment, this will be a glass-glass bond, but glass-plastic and plastic-plastic bonds may also be desired for some applications. Suitable adhesive include UV-curable acrylate adhesives such as Adhesive M36,427 type 68 (Edmund Scientific) or thermally-curable acrylic adhesives such as EPO-TEK 353ND (Epoxy Technology Inc.) Other suitable adhesive types are Duco Cement or 5-minute Epoxy (Thorlabs).

If the adhesive will come into contact with the gel upon filling the chamber, as in the embodiment depicted in FIG. 2, it is important to recognize that some adhesives will interfere with the polymerization of some gels. Thus, the use of a UV-curable adhesive in a holder for a UV-cured gel may not be ideal, because of interference between curing the adhesive and the gel. This problem does not arise in the embodiment shown in FIG. 2B where the adhesive is isolated from the gel chamber by the fiber pairs.

Figure 3:
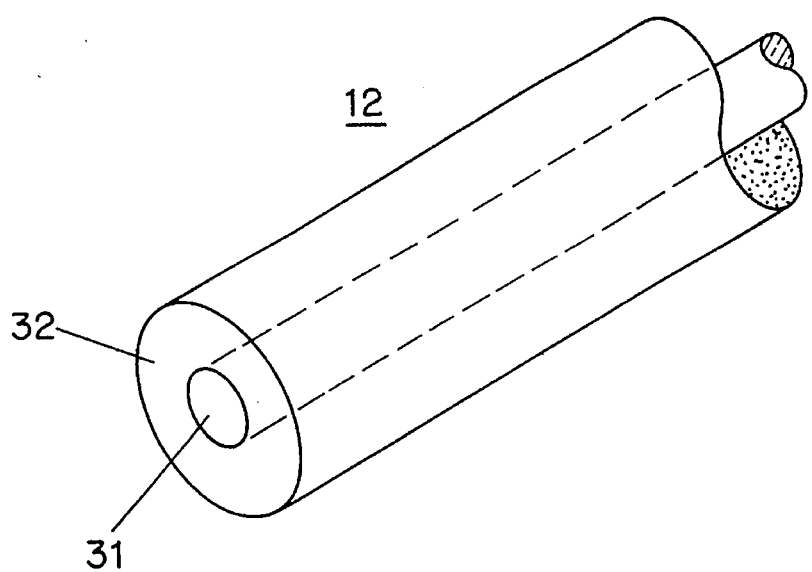
FIG. 3 shows an adhesive-coated fiber useful in the invention.

The gel holder of the invention can be made by using fibers which are coated with adhesive as shown in FIG. 3. These fibers have an interior core 31 made from a materials which can effectively define the spacing between the substrates. Suitable materials are glass, and substantially non-compressible polymeric materials such as nylon. The fibers are coated with a layer 32 of an adhesive. This layer should have a thickness which provides sufficient adhesive to ensure bonding of the fibers to the substrates, but not so great that adhesive blocks any significant part of the gel chamber. Suitable thicknesses are from 5 to 20 microns. The fiber materials and the adhesive should be selected so that they do not negatively impact on the ability of a gel to polymerize within the chamber nor fluoresce strongly at the wavelength used for detection of separated materials during or after electrophoresis.

The substrates used in forming the gel holders of the present invention may be any flat, planar material which is compatible with the electrophoresis gel and the method of detection to be employed. Thus, in some cases, plastic materials which do not interfere with the polymerization of the electrophoresis gel or the observation of the separated fragments on the electrophoresis gel can be used. Preferably, however, the substrates are made from glass, and most preferably from low-fluorescing glass. 1 mm Borosilicate glass which has greater ultraviolet light transparency is another preferred material.

Figure 4:
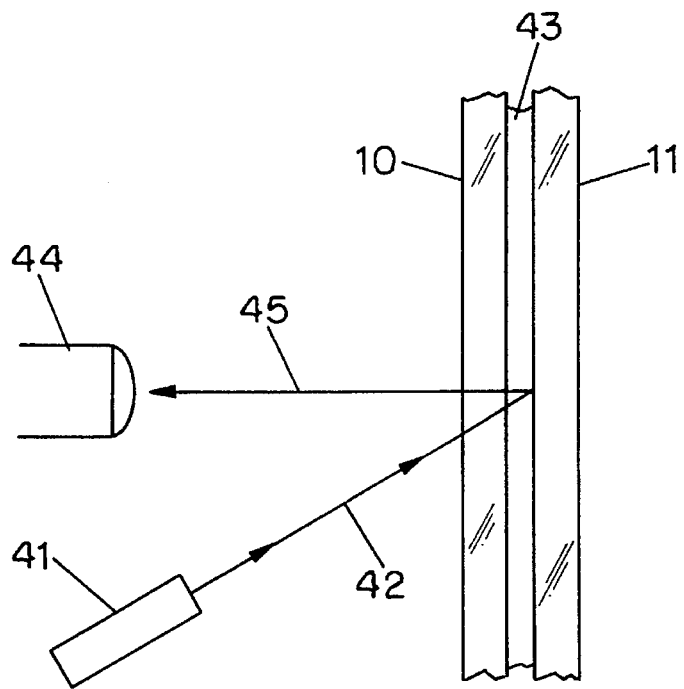
FIG. 4 shows an embodiment of the invention useful in apparatus where the interrogating beam and the detection system are on the same side of the gel.

At least one of the substrates used in forming the gel holder of the invention must be made from a material which will permit observation of the materials separated within the electrophoresis gel. In some apparatus, however, the interrogating beam source, for example a laser 41 producing a beam of light 42 for exciting fluorescent molecules in the gel 43, and the detector 44 for detecting emitted light 45 are located in the same side of the electrophoresis gel as shown in FIG. 4. In this case, the bottom substrate 11 can be selected to minimize any contribution to background radiation rather than for its ability to permit observation of the sample. For example, in the case of a gel holder intended for use in a sequencing apparatus with a fluorescence detection system, the bottom substrate 11 can be made from a colored glass which absorbs all of the exciting light which reaches it, and which thus is essentially non-fluorescent. Since background fluorescence arises in large part from fluorescent impurities in the substrates, this can substantially reduce the amount of background fluorescence and improve the sensitivity of the observations.

Figure 5:
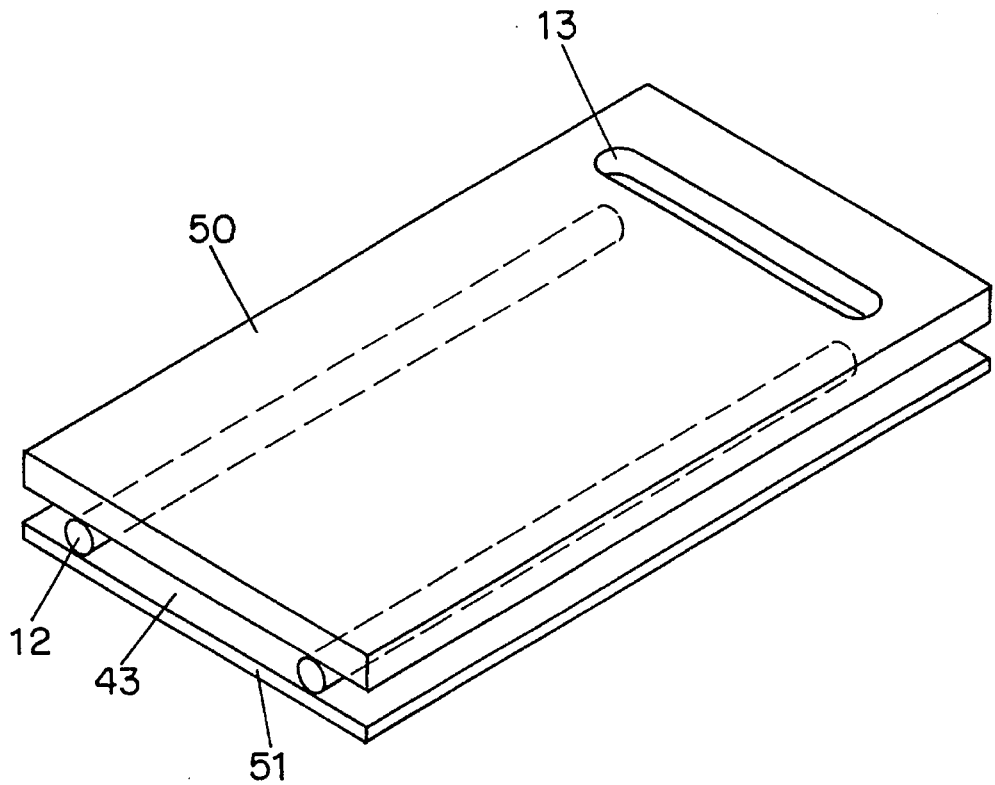
FIG. 5 shows an electrophoresis gel according to the invention.
Figure 6A:
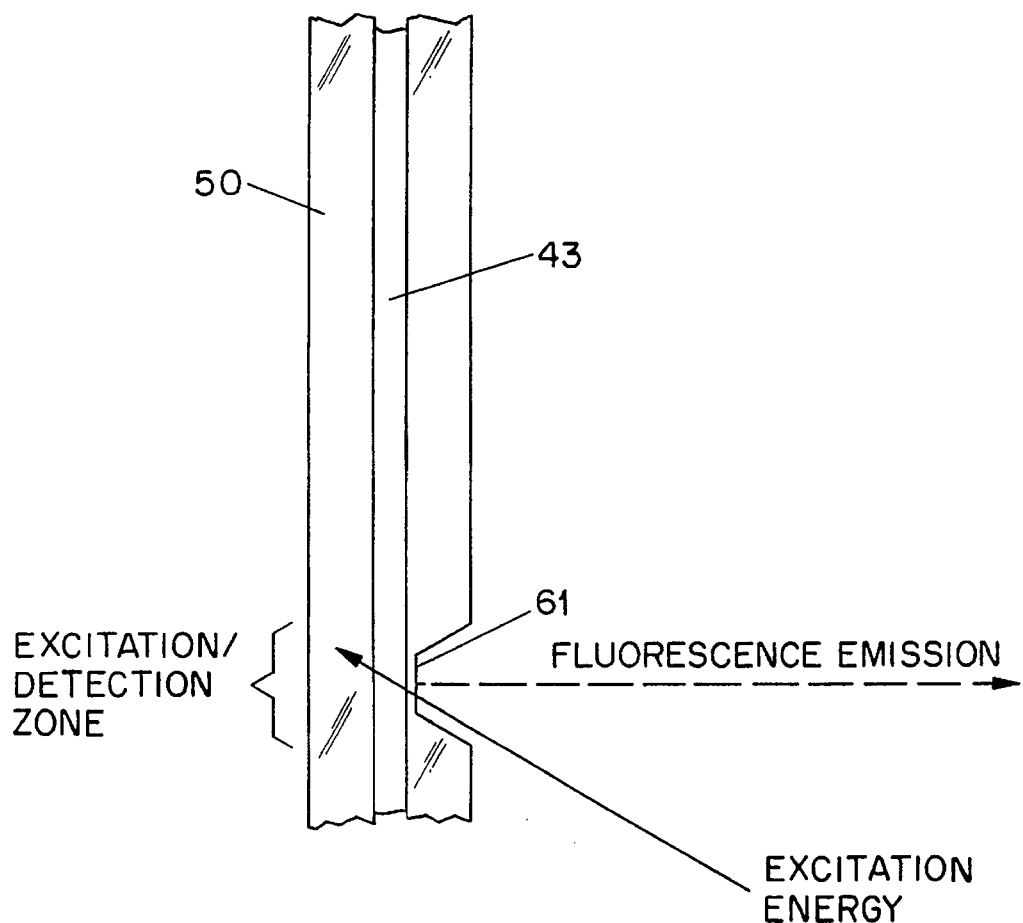
FIG. 6A and 6B show the use of thin regions in gel holders according to the invention.
Figure 6B:
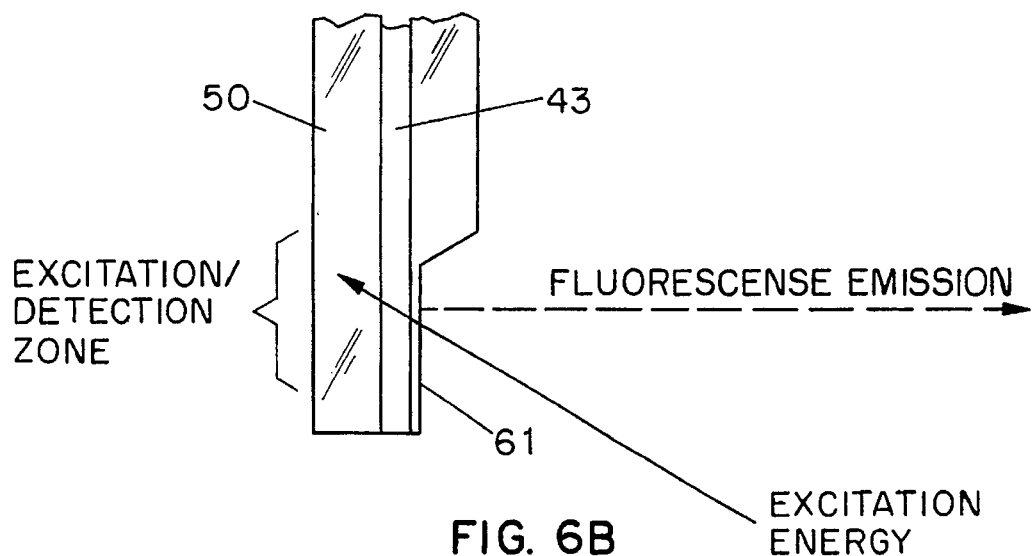
Figure 7A:
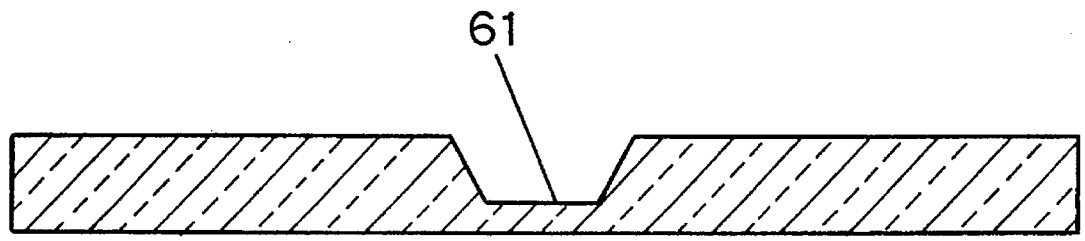
FIG. 7A and 7B show construction alternatives for substrates with thin regions.
Figure 7B:
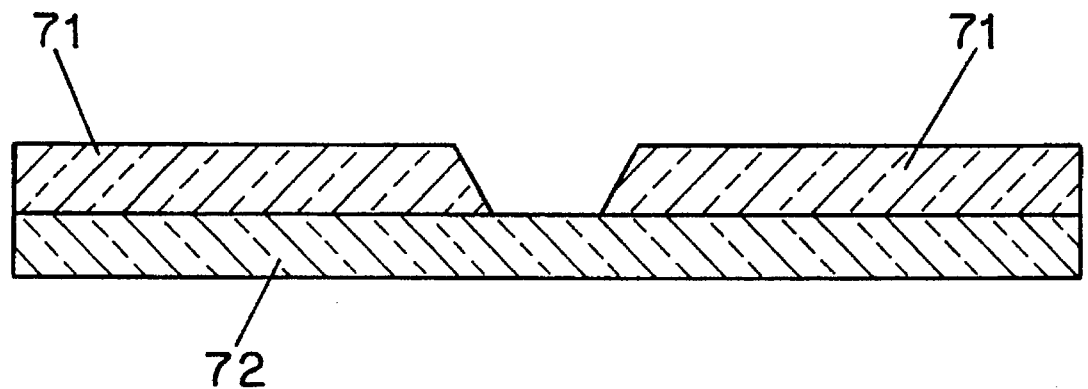

Another approach to reducing the background fluorescence is to utilize thinner substrates for the transparent substrate. For example, as shown in FIG. 5, one substrate 50 can be made of thicker (and preferably absorbing and non-fluorescing) material while the other substrate 51 is made of a very thin (i.e., 0.1 mm or less) transparent, low fluorescing material. Suitable thin materials include "cover slip" glass. The thin region 61 may also be localized to just an excitation/detection zone running perpendicular to the fibers as shown in FIG. 6A, or cover one edge of the gel as shown in FIG. 6B. Such substrates can be formed by molding a contiguous substrate into the desired shape (FIG. 7A), or by affixing blocks 71 of thicker materials onto a continuous thin substrate 72 (FIG. 7B). In the latter case, the blocks 71 of thicker material may also be formed from absorbing, non-fluorescing materials to further reduce background fluorescence.

To form the gel holder using adhesive-coated fibers, the coated fibers are first placed onto a surface of one of the substrates. The substrates should be aligned parallel to one another and parallel to two opposing edges of the substrate. Fibers can be placed in a frame which will keep them parallel to each other and positioned at a certain distance from each other. If two fibers are used, they are advantageously placed near the edges of the substrate, thus creating one large gel chamber in the interior. More than two fibers may be used, in which case the gel chamber is divided into several parts. In this instance, fibers are preferably placed at intervals such that each part of the chamber is large enough to receive four samples, i.e., one sample lane for each chain terminating oligonucleotide mixture used in the sequencing process. Thus, in a gel intended to have 16 lanes (4 complete sequences), a total of five fibers would be used. The use of more than two fibers is particularly suitable for wider gels since the interior fibers help prevent sagging of the substrate in the middle of the gel chamber and thus define a gel chamber of more consistent width.

In one embodiment of the method of the invention, the next step is to place the second substrate over the adhesive-coated fibers to form a sandwich structure in which the fibers are disposed between the two substrates. The substrates are brought into contact with the fibers on either side of the fiber array. Sufficient pressure is applied to secure the fibers to the substrates in a sandwich format, and the sandwich is then cured in a manner which will depend on the adhesive used. For example, if the adhesive used is EPO-TEK ND, curing can be achieved at 80° C. for 15 minutes or at 100° C. for 5 minutes. After the curing process is finished, lengths of fibers which extend beyond the edges of the substrates are cut off with a clipper or other means.

In a second embodiment of the method of the invention, the fibers are bonded to the first substrate prior to placing the second substrate over the fibers. For example, curing of a UV-activated adhesive may be initiated prior to the placement of the second substrate over the fibers. The second substrate is then placed on top of the partially melted fibers, and the substrates are pressed together and the adhesive is allowed to cure.

To form a gel holder with the configuration shown in FIG. 2B, pairs of fibers may be held in the desired array, suspended in the air by an external frame. Fibers are paired leaving a narrow gap between of the fibers of 0.5 mm to 2.5 mm. The gap is determined by the width of adhesive needed to secure the substrates together. The fiber array is placed onto one of the planar substrates. When the fibers are in the appropriate position, the space in between the fibers is filled with viscous adhesive, for example an epoxy adhesive such as EPO-TEK 353ND. The second substrate is then lowered onto the fiber array to form a sandwich. The sandwich is then cured, optionally under pressure and any fibers extending beyond the substrates are trimmed.

The size of the gel chamber in the gel holders of the invention is determined by the thickness of the interior core of the fibers. For applications in rapid sequencing of nucleic acids, these fibers will preferably have a diameter of 250 microns or less, and most preferably of 50 to 100 microns. It will be appreciated, however, that the lower limit is fixed only by the ability to obtain a very thin fiber of consistent core diameter and the ability to uniformly introduce a gel forming solution without bubble formation into significantly smaller gaps. In fact, the present invention provides a very facile way to achieve very small spacings between the substrates, regardless of the size of the gap. Similarly, it will be appreciated that the method of the invention can be used to make gel holders having a larger gap. Such gel holders are not as well suited to high speed analysis of nucleic acid fragments, however.

Once the gel holder has been formed using either of the methods described above, the next steps are the filling of the chamber with a gel forming solution and the polymerization of the solution to form a gel. This process can be performed in any of a number of ways which will be apparent to persons skilled in the art. Preferably, the gel holder is filled using an apparatus of the type described in U.S. patent application No. 08/332,892, filed Nov. 1, 1994, now U.S. Pat. No. 5,507,934 and International Patent Application No. PCT/US95/13954, filed Oct. 31, 1995, and published as WO96/13715, which application are incorporated herein by reference.

In a further embodiment of the invention, the gel is placed in the chamber prior to the application of the second substrate over the fibers. In this embodiment, the fibers are placed singly or in pairs over the first substrate, which may be light absorbing and non-fluorescing, and adhered to the substrate. A gel forming solution is then poured onto the substrate to essentially the same depth as the fibers and polymerized. Temporary glass plates may be attached from the sides to prevent the gel from running off. Alternatively, a frame may be used which tightly seals the edges into which the bottom substrate is positioned before and during polymerization. Because the top surface of the gel is free, this method provides a gel with very uniform thickness. After the gel is polymerized, a very thin, (i.e,. 1 to 10 microns) flexible and transparent film is laid onto the top of the gel and secured by adhesive or mechanical means. Suitable materials for use as the cover film include any dissolved polymers, and preferably those that are sprayable. The polymer film will not affect the polymerization of the gel, because the polymerization process is complete before the film is created.

The gel holders and electrophoresis gels of the present invention provide several advantages over the prior art. First, they are easy to manufacture, and can be prepared as disposable units for later filling with an electrophoresis gel. Second, they provide highly uniform spacing between the substrates. In addition, because the melt-flowed material is molded into shape thermally, materials such as glass which do not interfere with the polymerization of the gel or fluoresce strongly can be used to adhere the gel holders together.

We claim:

1. A method for forming a gel holder for an electrophoresis gel comprising the steps of:
   (a) placing a plurality of fibers between a first planar substrate and a second planar substrate; and
   (b) adhering the fibers to substrates with an adhesive, thereby forming a gel chamber between said first and second substrates, said gel chamber having a thickness defined by the fibers.

2. The method of claim 1, wherein the fibers are made from glass.

3. The method of claim 1, wherein the fibers have a diameter of 250 microns or less.

4. The method of claim 1, wherein the fibers are coated with the adhesive prior to being placed between the substrates.

5. The method of claim 4, wherein the adhesive-coated fibers are placed on a surface of the first planar substrate, the second planar substrate is placed over the fibers to form a sandwich in which the fibers are disposed between the first and second planar substrates; and pressure is applied to the substrates to form adhere the fibers to the substrates.

6. The method of claim 5, wherein the fibers are made from glass.

7. The method of claim 4, wherein the adhesive-coated fibers are placed on a surface of the first planar substrate and exposed to light to activate the adhesive; the second planar substrate is placed over the activated adhesive-coated fibers to form a sandwich in which the fibers are disposed between the first and second planar substrates; and pressure is applied to the exterior of the sandwich during curing of the adhesive.

8. The method of claim 7, wherein the fibers are made from glass.

9. The method of claim 1, wherein the fibers are laid down in pairs, each pair having a small space therebetween, and wherein the adhesive is disposed entirely in the small spaces between the pairs of fibers.

10. A gel holder for an electrophoresis gel, comprising:
   (a) a first planar substrate;
   (b) a second planar substrate;

(c) a plurality of fibers disposed between the first and second planar substrates, said fibers being adhered to the first and second planar substrates with an adhesive, and said fibers and said first and second planar substrates in concert defining a gel chamber having a thickness defined by the diameter of the fibers.

11. The gel holder of claim 10, wherein the fibers are glass.

12. The gel holder of claim 22, wherein the fibers have a diameter of 250 microns or less.

13. The gel holder of claim 10, wherein the first substrate and the second substrate have different optical properties.

14. The gel holder of claim 13, wherein one of the substrates is light absorbing and non-fluorescent.

15. The gel holder of claim 10, wherein one of the substrates is thinner than the other substrate.

16. The gel holder of claim 10, wherein one of the substrates has a thin region disposed near one end thereof extending perpendicular to the fibers.

17. The gel holder of claim 10, wherein the fibers are laid down in pairs, each pair having a small space therebetween, and wherein the adhesive is disposed entirely in the small spaces between the pairs of fibers.

18. The gel holder of claim 17, wherein the fibers are glass.

19. The gel holder of claim 17, wherein the fibers have a diameter of 250 microns or less.

20. The gel holder of claim 17, wherein the first substrate and the second substrate have different optical properties.

21. The gel holder of claim 20, wherein one of the substrates is light absorbing and non-fluorescent.

22. The gel holder of claim 17, wherein one of the substrates is thinner than the other substrate.

23. The gel holder of claim 17, wherein one of the substrates has a thin region disposed near one end thereof extending perpendicular to the fibers.

24. The gel holder of claim 1, wherein the fibers have a circular cross-section.

25. A method for forming an electrophoresis gel comprising the steps of:
   (a) placing a plurality of fibers between a first planar substrate and a second planar substrate;
   (b) adhering the fibers to substrates with an adhesive, thereby forming a gel chamber between said first and second substrates, said gel chamber having a thickness defined by the fibers; and
   (c) filling the gel chamber with an electrophoresis gel.

26. The method of claim 25, wherein the fibers are coated with the adhesive prior to being placed between the substrates.

27. The method of claim 26, wherein the adhesive-coated fibers are placed on a surface of the first planar substrate, the second planar substrate is placed over the fibers to form a sandwich in which the fibers are disposed between the first and second planar substrates; and pressure is applied to the substrates to form adhere the fibers to the substrates.

28. The method of claim 26, wherein the adhesive-coated fibers are placed on a surface of the first planar substrate and exposed to light to activate the adhesive; the second planar substrate is placed over the activated adhesive-coated fibers to form a sandwich in which the fibers are disposed between the first and second planar substrates; and pressure is applied to the exterior of the sandwich during curing of the adhesive.

29. The method of claim 25, wherein the fibers are laid down in pairs, each pair having a small space therebetween, and wherein the adhesive is disposed entirely in the small spaces between the pairs of fibers.

30. An electrophoresis gel, comprising:
   (a) a first planar substrate;
   (b) a second planar substrate;
   (c) a plurality of fibers disposed between the first and second planar substrates, said fibers being adhered to at least the first planar substrate with an adhesive, said fibers and said first and second planar substrates in concert defining a gel chamber having a thickness defined by the diameter of the fibers; and
   (d) a polymerized gel disposed within the gel chamber.

31. The electrophoresis gel of claim 30, wherein the polymerized gel is polyacrylamide.

32. The electrophoresis gel of claim 30, wherein the first substrate and the second substrate have different optical properties.

33. The electrophoresis gel of claim 30, wherein one of the substrates is light absorbing and non-fluorescent.

34. The electrophoresis gel of claim 30, wherein one of the substrates is thinner than the other substrate.

35. The electrophoresis gel of claim 30, wherein one of the substrates has a thin region disposed near one end thereof extending perpendicular to the fibers.

36. A method for forming an electrophoresis gel comprising the steps of:
   (a) placing a plurality of fibers on a planar substrate,
   (b) adhering the fibers to the planar substrate with an adhesive;
   (c) introducing a gel forming solution onto the substrate to a depth substantially equal to the fibers;
   (d) polymerizing the gel forming solution to form a polymerized gel; and
   (e) applying a flexible thin cover over the polymerized gel.

* * * * *